United States Patent
Lee

(10) Patent No.: US 9,880,181 B2
(45) Date of Patent: Jan. 30, 2018

(54) METHOD FOR PREPARATION OF PURIFIED AUTOIMMUNE ANTIGEN POSITIVE SERUM

(71) Applicant: HOB BIOTECH GROUP SUZHOU CO., LTD., Suzhou, Jiangsu (CN)

(72) Inventor: Charles Lee, Jiangsu (CN)

(73) Assignee: HOB BIOTECH GROUP SUZHOU CO., LTD., Suzhou (CN)

( * ) Notice: Subject to any disclaimer, the term of this patent is extended or adjusted under 35 U.S.C. 154(b) by 0 days.

(21) Appl. No.: 14/906,264

(22) PCT Filed: Nov. 14, 2014

(86) PCT No.: PCT/CN2014/091115
§ 371 (c)(1),
(2) Date: Jan. 20, 2016

(87) PCT Pub. No.: WO2016/061861
PCT Pub. Date: Apr. 28, 2016

(65) Prior Publication Data
US 2016/0327581 A1 Nov. 10, 2016

(30) Foreign Application Priority Data
Oct. 17, 2014 (CN) .......................... 2014 1 0553407

(51) Int. Cl.
*G01N 33/96* (2006.01)
*C07K 16/06* (2006.01)
*G01N 33/531* (2006.01)
*G01N 33/564* (2006.01)
*C07K 19/00* (2006.01)

(52) U.S. Cl.
CPC ........... *G01N 33/96* (2013.01); *C07K 16/065* (2013.01); *C07K 19/00* (2013.01); *G01N 33/531* (2013.01); *G01N 33/564* (2013.01)

(58) Field of Classification Search
CPC .... G01N 33/96; G01N 33/531; G01N 33/564; C07K 16/06
See application file for complete search history.

(56) References Cited

U.S. PATENT DOCUMENTS

| 4,929,543 A | 5/1990 | Kientsch-Engel et al. |
| 5,478,753 A | 12/1995 | Wong et al. |
| 5,491,218 A * | 2/1996 | Brust .................. G01N 33/531 435/7.1 |
| 5,895,811 A | 4/1999 | Brust et al. |

FOREIGN PATENT DOCUMENTS

| CN | 1924579 A | 3/2007 |
| CN | 103018436 A | 4/2013 |

OTHER PUBLICATIONS

International Search Report of PCT Patent Application No. PCT/CN2014/091115 dated Feb. 27, 2015.

* cited by examiner

*Primary Examiner* — Shafiqul Haq

(57) ABSTRACT

The present invention relates to a method for preparation of purified autoimmune antigen positive serum. The method comprises steps of: using autoimmune antigen to immunize healthy animals, obtaining antiserum after blood sampling, and purifying the antiserum for obtaining positive serum, the step of purifying the antiserum for obtaining positive serum are as follows: affining and purifying the antiserum for obtaining IgG antibody; coupling the IgG antibody and human IgG Fc or human IgM Fc or human IgA Fc at a ratio of 1:1~2; separating and purifying the coupled solution for obtaining IgG-IgG Fc conjugates concentrated solution or IgG-IgM Fc conjugates concentrated solution or IgG-IgA Fc conjugates concentrated solution; and diluting the IgG-IgG Fc conjugates concentrated solution or the IgG-IgM Fc conjugates concentrated solution or the IgG-IgA Fc conjugates concentrated solution to a concentration of 0.5~1 μg/ml for obtaining the positive serum.

11 Claims, 1 Drawing Sheet

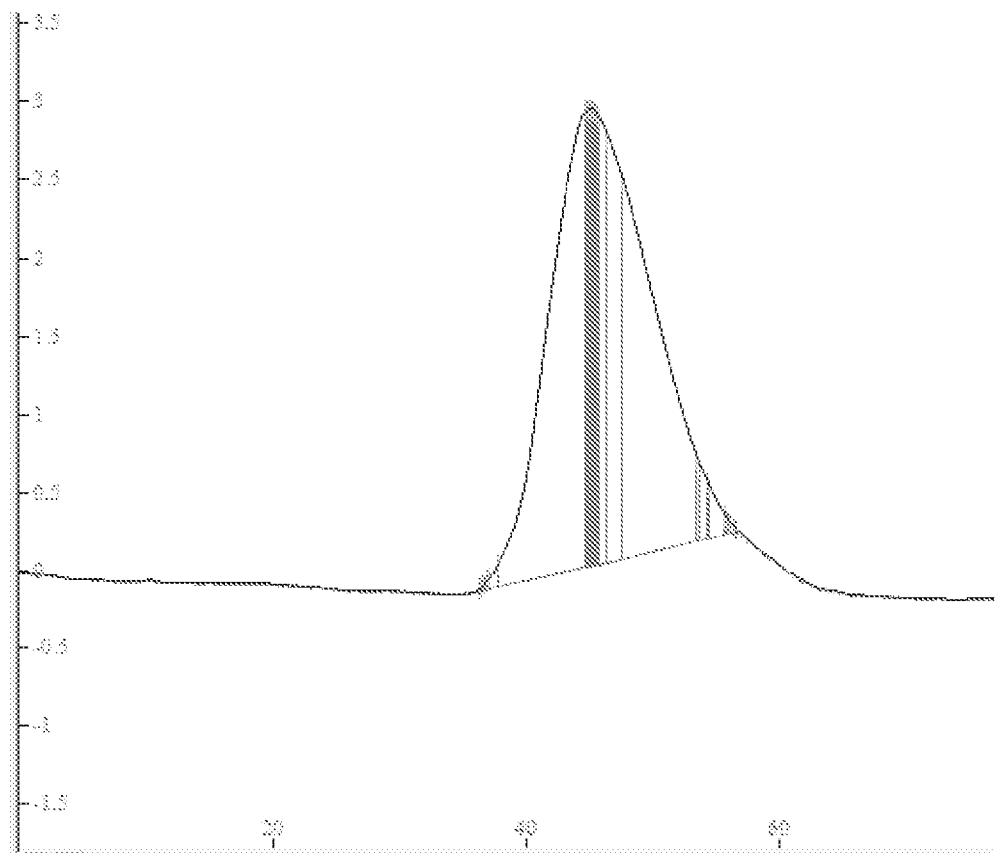

METHOD FOR PREPARATION OF PURIFIED AUTOIMMUNE ANTIGEN POSITIVE SERUM

FIELD OF THE INVENTION

The invention is related to a technology for in vitro diagnostic, specifically to the preparation of the autoimmune positive control serum.

BACKGROUND OF THE INVENTION

Under normal circumstances, the body recognizes and treats its own tissue components as "self", without immune response, which is self-tolerance. Self-tolerance occurs because the lymphocyte clones that recognize its own tissues are destroyed or forbidden during the embryonic development, as stated in Burnet's forbidden clone theory. However, in some cases, self-tolerance is compromised and the forbidden clones are re-activated, so that the body's immune system initiates immune response against its own tissue components, which leads to autoimmune diseases. The key is that the organism produces autoantibodies or sensitized T lymphocytes that react with its own tissue components and lead to the damage of the tissue and cells. The mechanism on the production of autoantibodies and sensitized T cells is very complicated. The following factors may play a role, according to research findings.

First, the Emergence of Autoantigen

1. Release of Sequestered Antigens

Sequestered antigens refer to tissue components, such as sperm, intraocular soluble components, brain tissue, etc, that normally do not contact with immune cells. However, their corresponding immune cell clones exist and are immune-responsive. When the isolation barrier is damaged due to surgery, trauma, infection and other reasons, the sequestered antigens are released into the bloodstream or lymph. The immune system mistake them as "foreign agents", trigger the autoimmune response, and result in the autoimmune disease.

2. Changes of Tissue Components

The antigenicity of tissue components may change due to physical factors (such as cold, heat, ionizing radiation), chemical factors (such as drugs), or biological factors (such as bacteria, viruses, etc.). The changed tissue components can stimulate an autoimmune response, and result in autoimmune diseases.

3. Cross-Reactivity

Some bacteria and viruses have similar epitopes as those on normal human tissue cells. The antibodies and sensitized lymphocytes produced against the foreign agents may cross react with the human epitopes, which finally result in autoimmune diseases.

Second, Abnormal Immune Response

1. Bypass Activation of Lymphocyte

Under normal circumstances, both autoantigen-specific T and B lymphocyte clones exist in the body. B lymphocytes can respond to autoantigens while the Th cells are irresponsive. With inactivated Th cells, B cells can't produce autoantibodies. Some foreign antigens have similar or identical determinants as those recognizable by B cells. Due to the difference of the carrier determinants recognized by various T cells, the Th cells that recognize autoantigens remain silent while those that recognize foreign agents are activated and in turn activate B cells to produce autoantibodies. Through this Th Bypass Activation, autoimmune response is initiated.

2. Bypass Activation of Polyclonal Stimulant

Some polyclonal stimulants, such as epstein-barr virus and super-antigens, are capable of initiating polyclonal activation of B-cells, or even of T-cells, by directly binding to the β-subunit of T-cell receptors in a non-specific fashion. Through this bypass activation, autoantibodies are produced and lead to the autoimmune response.

3. Abnormal Expression of Auxiliary Stimulating Factor

In the immune response, immune cell activation needs both the recognition by the immune active cells of the antigen peptide complex on the surface of the antigen presenting cells, and the interactions of auxiliary stimulating factors between the two cells. If the expression of the auxiliary stimulating factor on the surface of the antigen presenting cell is abnormal, this may activate the immune response of T cell and cause autoimmune diseases.

In addition, the imbalance of the functions of Th1 and Th2 cells are also related to the initiation of autoimmune diseases.

Third, Abnormal Expression of Fas/FasL

The abnormal expression of Fas/FasL is related to the genesis of autoimmune diseases. Fas belongs to the family of TNFR/NGFR (or CD95). It is present on the surface of a variety of cells including lymphocytes. Its ligand, FasL (Fas ligand), is usually expressed on the cellular membrane of the activated T cells such as CTL and NK cells. It can also be secreted into the extracellular space. Both free and membrane-bound FasL, when bind to membrane Fas, induce cell apoptosis. In the patients with Fas/FasL genetic defects, due to impaired apoptosis mechanism, the T and B lymphocyte clone proliferation is out of control, thus susceptible to various autoimmune diseases.

Fourth, Genetic Factors

Human autoimmune diseases often have family genetic predisposition. Research indicates that prevalence of many autoimmune diseases is correlated with detectability of certain HLA genotype. The correlation is mostly related to HLA-B or DR antigens.

For the development of allergy IVD, the positive control serum is an important tool, but the availability of positive sera for many autoantigens is very limited, if any. Approaches such as artificial sera have been attempted. For example, the patent CN103018436A published on Apr. 3, 2013, disclosed a method for preparing Infectious Bronchitis positive serum in rabbits. The whole blood from the immunized rabbit was centrifuged and filtered, and resulted in the positive serum. The crude preparation may result in low titers, which makes the artificial sera less valuable in the assay development.

SUMMARY OF THE INVENTION

The present invention is to provide a technical solution via a purification method in preparing high titer autoantigen positive sera.

The description of this method is as below:

A method for preparation of purified autoimmune antigen positive serum, wherein the method comprises steps of: using autoimmune antigen to immunize healthy animals, obtaining antiserum after blood sampling, and purifying the antiserum for obtaining positive serum, the step of purifying the antiserum for obtaining positive serum are as follows:

affining and purifying the antiserum for obtaining IgG antibody;

coupling the IgG antibody and human IgG Fc or human IgM Fc or human IgA Fc at a ratio of 1:1~2;

separating and purifying the coupled solution for obtaining IgG-IgG Fc conjugates concentrated solution or IgG-IgM Fc conjugates concentrated solution or IgG-IgA Fc conjugates concentrated solution; and diluting the IgG-IgG Fc conjugates concentrated solution or the IgG-IgM Fc conjugates concentrated solution or the IgG-IgA Fc conjugates concentrated solution to a concentration of 0.5~1 µg/ml for obtaining the positive serum.

Preferably, the antiserum is affined and purified by agarose affinity media, or immune affinity chromatography column.

Preferably, the agarose affinity medium is Protein-A sepharose CL-4B.

Preferably, the affinity chromatography column is prepared by coupling the autoimmune antigens to the sepharose gel.

Preferably, the antiserum is affined and purified by the immune affinity chromatography column after it is disposed by Ammonium sulfate.

Preferably, the human IgG Fc or the human IgM Fc or the human IgA Fc is prepared by the following steps:

firstly, dissolving the human IgG or the human IgM or the human IgA into papain digestive juices;

secondly, using the papain to digest the human IgG or the human IgM or the human IgA with digestion reaction;

thirdly, using iodoacetamide to terminate the digestion reaction;

finally, extracting the human IgG Fc or the human IgM Fc or the human IgA Fc through agarose affinity media.

Preferably, the IgG antibody and the human IgG Fc or the human IgM Fc or the human IgA Fc in the said IgG-IgE Fc conjugates was firstly activated by 2-imine tetrahydrothiophene coupling agent or 4-(N-maleic imide methyl) cyclohexane-1-carboxylic acid succinimide ester coupling agent, and then couple in condition of pH 7.2~7.4.

Preferably, a concentration of 2-imine tetrahydrothiophene coupling agent is 9~11 mg/ml, a concentration of 4-(N-maleic imide methyl) cyclohexane-1-carboxylic acid succinimide ester coupling agent is 4~6 mg/ml.

Preferably, the coupled solution is separated and purified using Sephadex 200 Gel purification column.

Preferably, the IgG-IgG Fc conjugates concentrated solution or the IgG-IgM Fc conjugates concentrated solution or the IgG-IgA Fc conjugates concentrated solution is diluted using a dilution buffer containing BSA 0.4~0.6%, Tris buffer 0.09~0.11 mol/L, and PH 7.5~8.5.

Due to the above described technical advancement, the present invention has the following advantages comparing to the existing technologies:

The production can be scaled up (from a few milliliters to several thousand milliliters) to suite the need, and effectively maintain the lot-to-lot consistency, which is unattainable with the crude positive serum preparation methods. In addition, the IgG Fc, the IgM Fc or the IgA Fc fragment is utilized to conjugate onto autoantigen specific IgG in the anti-serum, which conjugate molecules are much smaller than IgG-IgG, IgG-IgM or IgG-IgA, consequently decrease the cross reactivity and increase the specificity, and preserve the secondary antibody binding sites to a great extent.

The said method can be easily implemented to prepare positive sera for a variety of autoantigens. It solves the availability of positive sera in assay development and reagent manufacture, including calibrator preparation.

BRIEF DESCRIPTION OF THE DRAWINGS

The figure shows elution profile of IgG-IgG Fc conjugates from Sephacryl-200 gel purification column.

DESCRIPTION OF EMBODIMENTS OF THE INVENTION

The present invention will be further described in detail in conjunction with the specific embodiments below, but the present invention is not limited to the following examples. Conditions used in the example embodiments may be further adjusted according to different requirements of a particular use. Conditions that are not indicated in the example embodiments are common conditions.

Example 1

First: Rabbit autoantigen immunization and anti-serum titering

Materials and Equipment:

1. Autoantigen: lyophilized autoimmune antigen (Lc-1).
2. Adjuvant: Freund's complete adjuvant, Sigma (F5881); Freund's incomplete adjuvant, Sigma (F5506).
3. Animals: Three (for each autoantigen), two months old, 1.5-2.0 kg, healthy New Zealand rabbits.
4. The HRP-conjugated secondary antibody: HRP-conjugated goat anti-rabbit IgG.
5. Consumables: tee, disposable syringe, pipettes, etc.

Immunization Procedure:

1. Autoantigen preparation: Dissolve the autoantigen with PBS (to ensure the final conc. ranging 4-8 mg/ml), and measure protein concentration using the BCA protein quantification kit. Dilute 4 mg autoantigen to 600 µl, mix with complete or incomplete adjuvant (autoimmune antigen V: Adjuvant V=6:5). Emulsify the mixture by pushing through tee branch, till the drop into water is spherical without diffusion. Use Freund's complete adjuvant in the first immunization and Freund's incomplete adjuvantin the subsequent immunizations.

2. Animal Immunization: Keep the three newly purchased New Zealand rabbits in the animal room for one week; inject the autoantigen-adjuvant mixture subcutaneously in foot pad, neck and back using the 1 ml syringe; each rabbit receives injection at three points, with 300 µl per point; the immunization interval is 14 days.

3. Antiserum preparation: Draw 2 ml blood from each animal through the ear vein prior to immunization (blank), and once every 14 days post-immunization (Sample). Transfer the blood from the syringe slowly into a centrifuge tube and store overnight at 4° C., with the supernatant appearing yellowish. The antiserum is then transferred to another tube, centrifuge for 10 min at 1,500× g and combine the supernatants as antiserum. Aliquot and store the antiserum at −70° C.

4. Antisera is titered by ELISA. Autoantigen (Lc-1) is diluted in the coating buffer to 10 µg/ml. In each ELISA microplate, first two wells are coated with irrelevant proteins, 1 µg PCNA proteins and 1 µg Scl-70 proteins, respectively, as negative controls. The rest of wells are coated with 100 µl, 1 µg LC-1. Incubate for overnight at 4° C. After coating and washing, add 1:100 diluted rabbit anti-serum into the negative wells, followed with 3 blank control wells (Blank 1: serum prior to antigen injection; Blank 2: primary antibody blocking buffer; Blank 3: secondary antibody blocking buffer), and then serial dilution of rabbit anti-serum in the rest of wells. Finally, the enzyme-labeled goat anti-rabbit IgG antibody is added to determine the titer of rabbit anti-serum.

Each subsequent titer is measured against the one from the injection immediately preceding. If the two titers are insignificantly different, the animals are sacrificed to collect the blood.

Table 1 shows the results of titers of rabbit antisera post Lc-1 immunization.

TABLE 1

| Name | A OD value | B OD value |
|---|---|---|
| Negative Control One | 0.066 | 0.073 |
| Negative Control Two | 0.072 | 0.069 |
| Blank Control One | 0.065 | 0.066 |
| Blank Control Two | 0.072 | 0.075 |
| Blank Control Three | 0.068 | 0.065 |
| 1:100 | 3.401 | 3.359 |
| 1:200 | 3.357 | 3.321 |
| 1:400 | 3.279 | 3.173 |
| 1:800 | 2.987 | 2.997 |
| 1:1600 | 2.873 | 2.816 |
| 1:3200 | 2.432 | 2.653 |
| 1:6400 | 1.754 | 1.697 |
| 1:12800 | 0.897 | 0.902 |
| 1:25600 | 0.532 | 0.553 |
| 1:51200 | 0.299 | 0.279 |
| 1:102400 | 0.175 | 0.189 |
| 1:200000 | 0.093 | 0.103 |
| 1:400000 | 0.065 | 0.066 |
| 1:800000 | 0.068 | 0.066 |
| 1:1600000 | 0.065 | 0.067 |

Note:
A, titer post the 6$^{th}$ injection; B, titer post the 7$^{th}$ injection.

Above data show that the titers between post 6$^{th}$ and 7$^{th}$ injection are very similar and appear to be stable. The positive results have OD values twice that of the blank, such as the 1:51,200 dilution, while the negative results have OD values less than twice that of the blank. Negative controls have OD values equivalent to those of the blanks, confirming that this antiserum is not reacting with irrelevant autoantigens. Blanks have low OD values confirming that LC-1 has no non-specific reaction with pre-immunization rabbit serum or the buffers. The reaction from the rest of the wells is specific between LC-1 and rabbit anti-LC-1 sera, with OD values correlate with the dilution factor.

Second: Affinity purification of rabbit anti-autoantigen polyclonal antibody

Materials and Equipment:
1. Protein A sepharose CL-4B; peristaltic pump; centrifuge tube; centrifuge; filter; glass column.
2. TBS buffer: Dissolve 6.06 g Tris (50 mM), 8.78 g NaCl (150 mM) and 0.5 g sodium azide (0.05%) in 1 L distilled water; adjust to pH7.4 with HCl.
3. Neutralization buffer: Dissolve 121.2 g Tris (1 M), 87.8 g NaCl (1.5 M), 0.37 g EDTA (1 mM) and 5 g sodium azide (0.5%) in 1 L distilled water; adjust to pH8.0 with HCl.
4. Elution buffer (pH 2.7): Dissolve 3.75 g glycine (50 mM) in 1 L distilled water; adjust to pH 2.7 with HCl.
5. Elution buffer (pH 1.9): Dissolve 3.75 g glycine (50 mM) in 1 L distilled water; adjust to pH 1.9 with HCl.

Procedure:
1. Mix equal volumes of resin and TBS buffer in a vacuum flask. Mix under vacuum for about 15 minutes to remove air bubbles in the resin. The protein A sepharose CL-4B resin is slowly transferred into the glass column, control the fill rate of 1-2 ml/min with a pump, then equilibrate the column using ten times the bed volume of ice-cold TBS buffer.
2. Place the antiserum at 4° C. to thaw slowly to avoid the protein aggregation. If aggregation occurs in the thawing process, place the tube at 37° C. to warm-up and dissolve aggregates. Sodium azide is added to 0.05%, centrifuge at 4° C. 15,000×g for 5 minutes, transfer the supernatant and filtrate to remove excess fat.
3. Dilute the thawed antiserum at 1:5 (v/v) with TBS buffer, and then filtrate. Add the antiserum onto the column at a rate of 0.5 ml per minute. The antiserum should be applied twice and the flow through is to be collected. Wash the column with TBS buffer till $A_{\lambda 280\ nm}$<0.008. The bound protein was eluted by the elution buffer (pH2.7) at 0.5 ml/min. Collect the elutent into 1.5 ml EP tube which has 100 μl neutralize buffer solution. Mix and check the eluent pH with pH test paper, if the pH<7, adjust to about pH7.4 with neutralize buffer solution to prevent antibody degeneration.

Add 10 ml, pH1.9 elution buffer in the column, and collect the eluate until $A_{\lambda 280\ nm}$<0.008 as described above.

Measure the protein concentration with a spectrophotometer. If the protein concentration is less than 0.5 mg/ml, add 10% glycerol. Aliquot and store the purified antibody at 2-8° C.

Wash the column with TBS-NaN3, and store the column at 2° C.-8° C.

Third: Conjugation of IgG with human IgG Fc

Materials and Equipment
1. The human IgG Fc, produced in HOB Biotech Group Co. Ltd, stored in phosphate buffer.
2. Papain Buffer: 0.1 M Tris, 2 mM EDTA, pH8.0.
3. Papain and Iodoacetamide, Sigma; Protein-A, GE;
4. SMCC and Traut's reagent, Thermo; TRIS and other chemical reagents, chemical purity;
5. G-25 gel column and Supperdex 200 gel purification column, GE.

Procedure
1. Dissolve the human IgG into Papain buffer, add Papain to start and Iodoacetamide to stop the reaction, then purify human IgG Fc with protein-A.
2. Transfer 1 mg rabbit-anti IgG, add 3 μl 10 mg/ml coupling reagent 2-IT solution, incubate at room temperature for 20 min; add 10 μl 0.1 mol/L glycine solution, incubate at room temperature for 5 min. Desalt with G-25 gel column, collect the activated antibody, and store at 5° C.;
3. Transfer 1.5 mg human IgG Fc, add 15 μl 5 mg/ml SMCC, incubate at room temperature for 30 min. Desalt with G-25 gel column, collect the activated antibody, store at 5° C.;
4. Mix the above-activated IgG antibody and human IgG Fc, react at pH 7.3 for 20 h; purify the conjugate with Sephacryl-200 gel purification column, and store at 5° C.;
5. Dilute the IgG-IgG Fc conjugate stock solution with 0.1 mol/L pH 8.0Tris buffer (containing 0.5% BSA) to 0.5 μg/ml.

Fourth: Use the autoantigen (Lc-1) antibody assay kit from EUROIMMUN to measure the titer of the positive serum. The results are shown in Table 2.

TABLE 2

| Name | Dilution factor | EUROIMMUN Results |
|---|---|---|
| IgG-IgE FC (Lc-1) LOT 140325 | Neat | >400 RU/mL |
|  | 1:3 | 307 RU/mL |
|  | 1:9 | 110 RU/mL |
| IgG-IgE FC (Lc-1) LOT 140513 | Neat | >400 RU/mL |
|  | 1:3 | 355 RU/mL |
|  | 1:9 | 140 RU/mL |
| IgG-IgE FC (Lc-1) LOT 140719 | Neat | >400 RU/mL |
|  | 1:3 | 270 RU/mL |
|  | 1:9 | 105 RU/mL |

Note:
EUROIMMUN's score system for autoimmune antibody IgG (IgM, IgA): the cutoff value is 20 RU/mL.

Data in Table 2 show that the three batches (LOT 140325, LOT 140513, LOT 140719) positive serum control samples are positive samples. The values are linearly correlated with the dilution factors. The preparation of IgG-IgG Fc conjugate, IgG-IgM Fc conjugate or IgG-IgA Fc conjugate as autoantigen-specific antisera have been successful and the samples can be used as controls for the assay kit.

Example 2

First, the immune of autoantigen and the titration of rabbit antisera

Material and Equipment

1. Autoantigen: lyophilized PCNA autoimmune antigen;
2. Adjuvant: Freund's complete adjuvant, Sigma (F5881); Freund's incomplete adjuvant, Sigma (F5506);
3. Animals: Three (for each antigen), two-month old, 1.5-2.0 kg, healthy New Zealand rabbits.
4. Second-antibody: AP-conjugated sheep anti-rabbit IgG;
5. Consumables: tee, disposable syringes, pipetting device and etc.

Immune Procedure

1. Autoantigen preparation: Dissolve the autoantigen with PBS and measure protein concentration using the BCA protein quantification kit. For the first immunization, dilute the autoantigen to 0.05 mg, 0.15 mg and 0.2 mg in 300 μL PBS, and mix with freund's complete adjuvant as 0.8:1 (v/v), by pipetting up and down for 10 times and use immediately. For the second immunization and on, dilute autoantigen to 0.05 mg, 0.15 mg and 0.2 mg in 500 μL PBS, and mix with freund's incomplete adjuvant at a rate of 0.8:1 (v/v), by pipetting up and down for about 10 times and use immediately.

2. Animal immunization: Keep three white New Zealand rabbits in the animal room for 1 week. In the first immunization, inject 0.5 ml mixture using a 1 ml syringe to the rabbit's foot. Later immunizations are performed through leg and breast muscle injection. The immunization interval is 7 days.

3. Antiserum preparation: Collect 2 mL blood from the ear vein prior to immunization (control), and once every two weeks post immunization (sample). When the tier meets requirements, collect large volume of blood through heart blood collection. The blood is centrifuged at 1000 rpm for 15 min. Aliquot and stored the antiserum at −70° C.

Antiserum titer determination: Use the microplate based chemiluminescence method to evaluate the antiserum. Dilute the autoantigen to 5 μg/ml in the coating buffer, and add 100 μL, 0.5 μg autoantigen per well except the negative wells, coating at 37° C. for 2 hours. The primary antibody is the serially diluted antiserum, and the secondary antibody is the sheep anti-rabbit IgG conjugated to AP. The negative control: serially diluted pre-immunization antiserum. Blank: use the blocking buffer. The antisera are serially diluted as 1:200, 1:400 till 1:100,000, meeting criteria.

The results in Tables 3 and 4 show the tittering results for the rabbit anti-PCNA-sera post immunization.

TABLE 3

| | Animal Serial No. 672 | | |
|---|---|---|---|
| Serum Serial No. | Positive A(RLU) | Positive B(RLU) | Negative(RLU) |
| Blank comparison | 31053 | 36392 | |
| 1:200 | 8806532 | 8652010 | 50214 |
| 1:400 | 7354210 | 7021584 | 40238 |
| 1:800 | 6653201 | 6782106 | 39654 |
| 1:1600 | 5539560 | 5301247 | 37042 |
| 1:3200 | 3921405 | 3762014 | 34410 |
| 1:6400 | 2735210 | 2684512 | 32587 |
| 1:12800 | 1532013 | 1498751 | 36951 |
| 1:25600 | 801452 | 889741 | 33084 |
| 1:51200 | 502487 | 498751 | |
| 1:102400 | 276301 | 268745 | |
| 1:204800 | 143012 | 130214 | |
| 1:409600 | 77951 | 69821 | |
| 1:800000 | 63120 | 59210 | |
| 1:1600000 | 44301 | 40287 | |
| 1:3200000 | 38795 | 39062 | |

TABLE 4

| | Animal Serial No. | | | | | |
|---|---|---|---|---|---|---|
| | 751 | | | 752 | | |
| Serum Serial No. | Positive A (RLU) | Positive B (RLU) | Negative (RLU) | Positive A (RLU) | Positive B (RLU) | Negative (RLU) |
| Blank comparison | 43201 | 39654 | | 39650 | 42651 | |
| 1:200 | 8462109 | 8657021 | 69874 | 7479512 | 7298745 | 57894 |
| 1:400 | 7024510 | 7345792 | 53214 | 6985497 | 6851246 | 53201 |
| 1:800 | 6521034 | 6210348 | 43210 | 5954125 | 5782106 | 49861 |
| 1:1600 | 5987412 | 5341258 | 39854 | 4032145 | 4468719 | 43210 |
| 1:3200 | 3987451 | 4021854 | 37951 | 2365410 | 2698512 | 42597 |
| 1:6400 | 2568741 | 2721466 | 38754 | 1325015 | 1603287 | 39654 |
| 1:12800 | 1458461 | 1398549 | 37210 | 892140 | 910234 | 41987 |
| 1:25600 | 832015 | 895412 | 39841 | 501235 | 498512 | 39875 |
| 1:51200 | 495223 | 478512 | | 298541 | 302158 | |
| 1:102400 | 298451 | 275130 | | 162013 | 176124 | |
| 1:204800 | 136892 | 149520 | | 86324 | 96541 | |

TABLE 4-continued

| Serum Serial No. | 751 Positive A (RLU) | 751 Positive B (RLU) | 751 Negative (RLU) | 752 Positive A (RLU) | 752 Positive B (RLU) | 752 Negative (RLU) |
|---|---|---|---|---|---|---|
| 1:409600 | 69851 | 70327 | | 63251 | 68745 | |
| 1:800000 | 59874 | 57846 | | 55201 | 53210 | |
| 1:1600000 | 46987 | 43296 | | 49875 | 46251 | |
| 1:3200000 | 37521 | 36501 | | 40123 | 39650 | |

TABLE 5

| Animal Serial No. | 750 | 751 | 752 |
|---|---|---|---|
| Antiserum titer | 1:200000 | 1:200000 | 1:100000 |

Note:
The antiserum titers are from 3 rabbits: A, post4$^{th}$immunization; B, post5$^{th}$ immunization.

Above data show that the titer of the antisera post the 4$^{th}$ injection meet the requirements and the tiers are greater than 1:100,000. According to the experimental design, the serum dilution ranges from 1:200 to 1:3200000. When RLU is above twice that of the negative control at 1:200 dilution (criteria for positive), the result is positive, otherwise negative. Rabbits 672, 671 and 670 antisera at 1:100,000 dilution, all have RLU above twice of the control, so all positive. Further dilution results in RLU below criteria, so becomes negative.

Second, antiserum affinity purification
Material and Equipment:
1. Equipment and supply: Immune affinity chromatography column, peristaltic pump and centrifugal pipe, centrifuge, filter, column chromatography, spectrophotometer;
2. TBS buffer: Dissolve 6.06 g Tris (50 mM), 8.78 g NaCl (150 mM), and 0.5 g sodium azide (0.05%) in 1 L distilled water, and adjust to pH 7.4 with HCl;
3. High salt buffer solution: Dissolve 121.2 g Tris (1 M), 87.8 g NaCl (1.5M), EDTA (1 mM) 0.37 g and 5 g sodium azide (0.5%) in 1 L distilled water, adjust to pH 8.0 with HCl;
4. Elution buffer: Dissolve 3.75 g glycine (50 mM) in 1 L distilled water, and adjust to pH 2.6 with HCl;
5. CNBr-actived Sepharose 4B-Cl, bought from GE, column materials storage solution (0.1 M PBS, 1% amino caproic acid, pH 7.4).

Operation Procedure
1. Immuno-affinity chromatography column: Couple the autoantibody onto the agarose gel to obtain the affinity chromatography column. Specific procedures are as following:

Dilute the specific autoantibody to 1.0 mg/ml with 0.2 M carbonate buffer (pH 9.5);

Treat the activated Sepharose 4B-Cl (CNBr-active Sepharose 4B-Cl) with 1.0 mM HCL, and dilute to 1.0 g/ml in the 0.2 M carbonate buffer (pH 9.5);

Mix the two parts at 1:1, and react at room temperature for 16 to 20 hours, centrifuge and collect the supernatant;

Measure protein concentration of the supernatant, subtract from the total to derive the amount of antigen coupled to the resin in the column.

Add the remaining Sepharose 4B-Cl into 1.0 M glycine solution at 1:1 ratio, react at room temperature for 4 hours. Wash the gel with 0.1 M HCl, 0.1 M NaOH and 2 M urea sequentially with 3 times column bed volume. Store the resin in the storage buffer.

2. Mix well at equivalent volumes the affinity chromatography resin and animal serum processed with the ammonium persulfate for 2 hours. Transfer the mixture slowly into the glass column, and control the filling rate at 1-2 ml/min with a pump and avoid the gel drying. Apply 3-10 bed volume of buffer to equilibrate the column.
3. Wash the column with TBS buffer till $A_{280\ nm}$<0.008. Then apply the high salt buffer to remove the nonspecifically bound proteins. The bound protein is eluted with the elution buffer (pH2.6) at 0.5 ml/min. Collect the eluent into 1.5 ml EP tubes prefilled with 100 μl neutralize buffer till $A_{280\ nm}$<0.008. Mix and check the eluent pH with pH test paper, if the pH<7, adjust to about pH7.4 with neutralization buffer to avoid antibody degeneration.

Measure the protein concentration with a spectrophotometer. If the protein concentration is less than 0.5 mg/ml, add 10% glycerol. Aliquot and store the purified antibody at 2-8° C. Wash the column with TBS (0.05% NaN3 added), and store the column at 2-8° C.

Third, Conjugation of IgG with human IgG Fc
Material and Equipment
1. The human IgG Fc, produced in HOB Biotech Group Co. Ltd, stored in phosphate buffer.
2. Papain Buffer: 0.1 M Tris, 2 mM EDTA, pH 8.0.
3. Papain and Iodoacetamide, Sigma; Protein-A, GE.
4. SMCC and Traut's reagent, Thermo; TRIS and other chemical reagents, chemical purity.
5. G-25 gel column and Supperdex 200 gel purification column, GE.

Operation Procedure
1. Dialyze human IgG is with 95% purity, 1 mg/ml into Papain Buffer (pH 8.0). Add Papain at a ratio of Papain: IgG=100:1 (w/w), and incubate for 30 min. Then add Iodoacetamide to stop the reaction. Purify human IgG Fc with protein A purification column
2. Add 15 μL of 5 mg/ml SMCC solution to 1 mg IgG antibody solution, and at room temperature incubate for 30 min. Use G-25 gel column to remove the free SMCC, and collect antibodies after activation, and store at 4° C.;
3. Mix 1.5 mg human IgG Fc with 3 μL coupling agent 2-IT solution at 10 mg/ml, and incubate at room temperature for 20 min. Then add 10 μL glycine solution at 0.1 mol/L, and incubate at room temperature for 5 min. Use G-25 gel column to remove the free 2-IT, and collect antibodies after activation, and keep at 4° C.;
4. Mix the said above-activated IgG antibody and human IgG Fc, react at pH 7.3 for 20 h; purify the conjugate with Sephacryl-200 gel purification column, and store at 4° C.;
5. Dilute the IgG-IgG conjugate stock solution to 0.5 μg/ml with 0.1 mol/L Tris buffer (containing 0.5% BSA, pH 8.0).

Fourth, use specific autoantigen (PCNA) IgG antibody test kits manufactured by EUROIMMUN to detect the positive serum in example 2. The results are shown in Table 6.

TABLE 6

| name | Dilution rate | EUROIMMUN Results |
|---|---|---|
| IgG-IgG FC (PCNA) LOT 140403 | Neat | >400 RU/ml |
| | 1:3 | 398 RU/ml |
| | 1:9 | 165 RU/ml |
| IgG-IgG FC (PCNA) LOT 140517 | Neat | >400 RU/ml |
| | 1:3 | 321 RU/ml |
| | 1:9 | 120 RU/ml |
| IgG-IgG FC (PCNA) LOT 140802 | Neat | >400 RU/ml |
| | 1:3 | 362 RU/ml |
| | 1:9 | 135 RU/ml |

Note:
EUROIMMUN autoimmune antigen IgG (IgM,IgA)testing:
The cut-off value is 20 RU/mL;
>20 RU/mL, positive;
<20 RU/mL, negative;

Data in Table 6 show that three batches of positive serum of quality control samples (LOT140403 LOT140517 LOT140802) are positive per EUROIMMUN autoantigen IgG test kits, and with 1:3 to 1:9 dilution, the positivity preserves. Also the values are linearly correlated with the dilution factors. The preparation of IgG-IgG Fc conjugate as autoantigen-specific antisera have been successful and the samples can be used as controls for the assay kit.

A detailed description of the invention is presented above, to make the content and implementation of the present invention understandable to the field, which should not place any limitation on the extent of protection of the present invention. All the spiritual essence of the equivalent change and modification according to the invention should be within the scope of protection of the present invention.

What is claimed is:

1. A method for preparation of purified autoimmune antigen positive serum, the method comprising the steps of immunizing a healthy animal with an autoimmune antigen, obtaining antiserum after blood sampling from the immunized animal, purifying the antiserum and obtaining positive serum, wherein the steps of purifying the antiserum and obtaining the positive serum are as follows:

Purifying IgG antibody from the antiserum obtained after the blood sampling by an affinity chromatography;

Preparing human IgG Fc, human IgM Fc or human IgA Fc fraction by digesting human IgG, human IgM or human IgA by papain followed by purification of human IgG Fc fraction, human IgM Fc fraction, or human IgA Fc fraction by protein A affinity chromatograph, and activating the purified Fc fraction by 4-(N-maleic imide methyl) cyclohexane-1-carboxylic acid succinimide ester;

coupling the purified IgG antibody with the activated human IgG Fc or the activated human IgM Fc or the activated human IgA Fc at a ratio of 1:1~2 to form a first coupled solution comprising IgG-IgG Fc conjugates or a second coupled solution comprising IgG-IgM Fc conjugates or a third coupled solution comprising IgG-IgA Fc conjugates respectively;

separating and purifying the IgG-IgG Fc conjugates as a concentrated solution from the first coupled solution or the IgG-IgM Fc conjugates as a concentrated solution from the second coupled solution or the IgG-IgA Fc conjugates as a concentrated solution from the third coupled solution; and diluting the IgG-IgG Fc conjugates concentrated solution or the IgG-IgM Fc conjugates concentrated solution or the IgG-IgA Fc conjugates concentrated solution to a concentration of 0.5~1 ug/ml which forms the positive serum.

2. The method of claim 1, wherein the antiserum is purified by agarose affinity media, or immune affinity chromatography column.

3. The method of claim 2, wherein the agarose affinity media is Protein-A sepharose CL-4B.

4. The method of claim 2, wherein the immune affinity chromatography is prepared by coupling the autoimmune antigen to sepharose gel.

5. The method of claim 2, wherein the antiserum is purified by the immune affinity chromatography column after it is disposed by Ammonium sulfate.

6. The method of claim 1, wherein the human IgG Fc or the human IgM Fc or the human IgA Fc is prepared by the following steps:

firstly, dissolving the human IgG or the human IgM or the human IgA into a papain buffer;

secondly, adding the enzyme papain to the papain buffer to digest the human IgG or the human IgM or the human IgA and carrying out digestion reaction;

thirdly, after the digestion reaction, adding iodoacetamide to terminate the digestion reaction, and finally, after the termination step, extracting the human IgG Fc or the human IgM Fc or the human IgA Fc with the protein A affinity chromatography.

7. The method of claim 1, wherein the IgG antibody and the human IgG Fc or the human IgM Fc or the human IgA Fc is activated by 4-(N-maleic imide methyl) cyclohexane-1-carboxylic acid succinimide ester, and coupled at pH 7.2-7.4.

8. The method of claim 7, wherein the concentration of 4-(N-maleic imide methyl) cyclohexane-1-carboxylic acid succinimide ester coupling agent is 4~6 mg/ml.

9. The method of claim 1, wherein the first coupled solution or the second coupled solution or the third coupled solution is separated and purified using Sephadex 200 Gel purification column.

10. The method of claim 1, wherein the IgG-IgG Fc conjugates concentrated solution or the IgG-IgM Fc conjugates concentrated solution or the IgG-IgA Fc conjugates concentrated solution is diluted using a dilution buffer containing BSA 0.4~0.6%, Tris buffer 0.09~0.11 mol/L, and PH 7.5~8.5.

11. The method of claim 4, wherein the antiserum is purified by the immune affinity chromatography column after it is disposed by Ammonium sulfate.

* * * * *